US00PP11390P

United States Patent [19]

Heims

[11] Patent Number: Plant 11,390

[45] Date of Patent: May 23, 2000

[54] HEUCHERA PLANT NAMED 'MAGIC WAND'

[75] Inventor: Dan M. Heims, Portland, Oreg.

[73] Assignee: Terra Nova Nurseries, Inc., Tigard, Oreg.

[21] Appl. No.: 09/103,650

[22] Filed: Jun. 23, 1998

[51] Int. Cl.[7] ..... A01H 5/00

[52] U.S. Cl. ..... Plt./263

[58] Field of Search ..... Plt./263

[56] References Cited

PUBLICATIONS

GTITM UPOVROM Citation for 'Magic Wand' as per QZ PBR 980693.

*Primary Examiner*—Howard J. Locker
*Assistant Examiner*—Kent L. Bell
*Attorney, Agent, or Firm*—Klarquist Sparkman Campbell Leigh & Whinston, LLP

[57] ABSTRACT

A new and distinct hybrid of Heuchera plant characterized by unique flower panicles, attractive leaf coloration, and large flowers.

2 Drawing Sheets

The present invention relates to a new and distinct hybrid of Heuchera in the Saxifrage family (Saxifragaceae) which originated as a cross-pollination of an unnamed, unpatented Heuchera hybrid seedling (female parent) and a selected unnamed, unpatented *Heuchera sanguinea* plant (male parent) showing brilliant coloration.

The new Heuchera is a result of a controlled cross of the aforementioned plants at Terra Nova Nursery, Inc., in Canby, Oreg. This hybrid was selected from a large selection of seedlings. Seed and pollen parent plants were retained to observe habit and to compare with the new variety. The new variety has been reproduced only by asexual propagation (division and tissue culture). Each of the progeny exhibits identical characteristics to the original plant and is unlike any Heuchera offered by any American nursery or book known to me as evidenced by the following characteristics:

(1) Late summer, fall and winter: Attractive mottled foliage.

(2) Spring/Early summer: Colorful flowers on hirsute panicles.

Asexual propagation by division and tissue-culture as done in Tigard, Oreg., shows that the foregoing characteristics and distinctions come true to form and are established and transmitted through succeeding propagations.

BRIEF DESCRIPTION OF THE PHOTOGRAPHS

Figure 1:
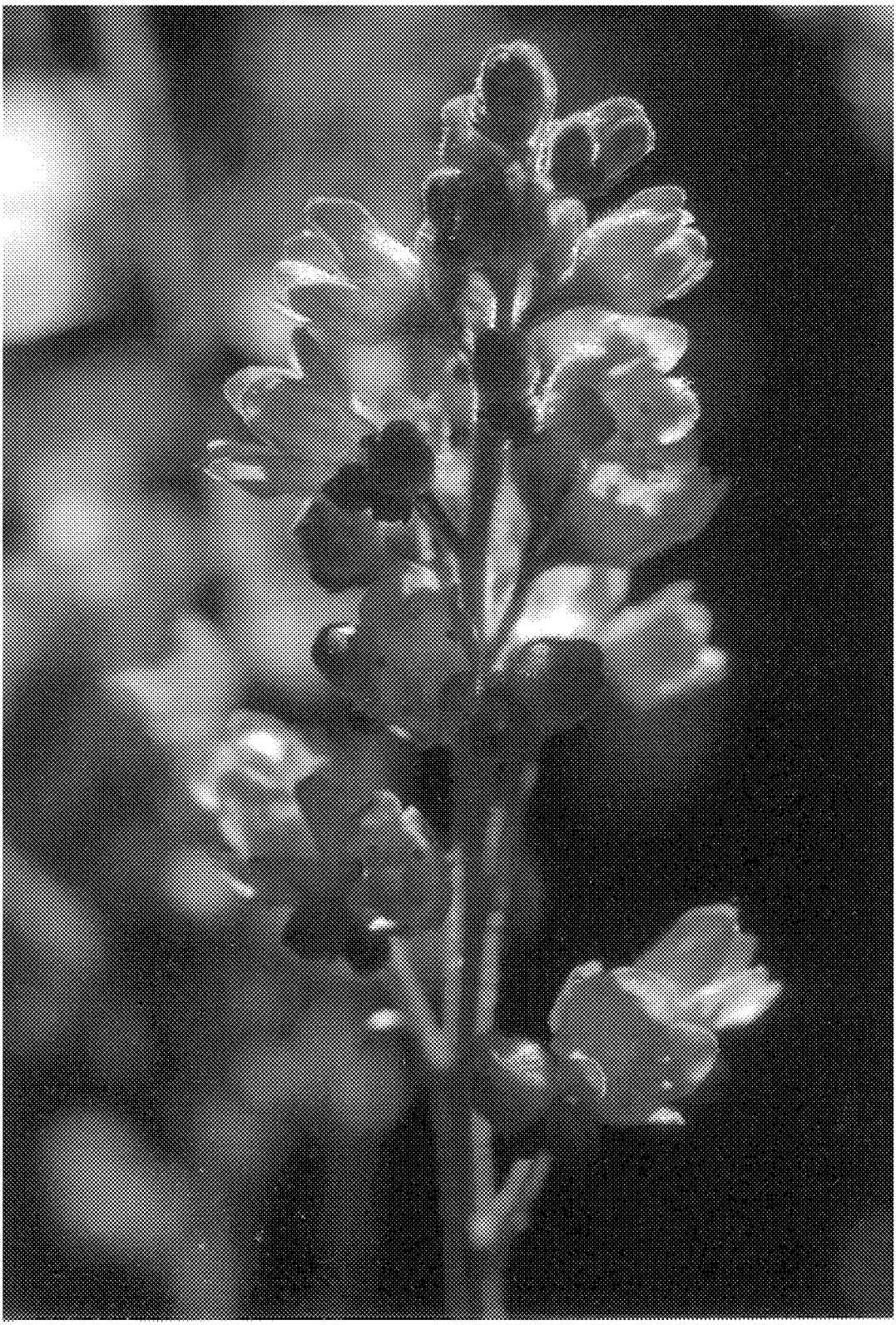
FIG. 1 is a close-up showing the flowers of a mature plant in Canby, Oreg.
Figure 2:
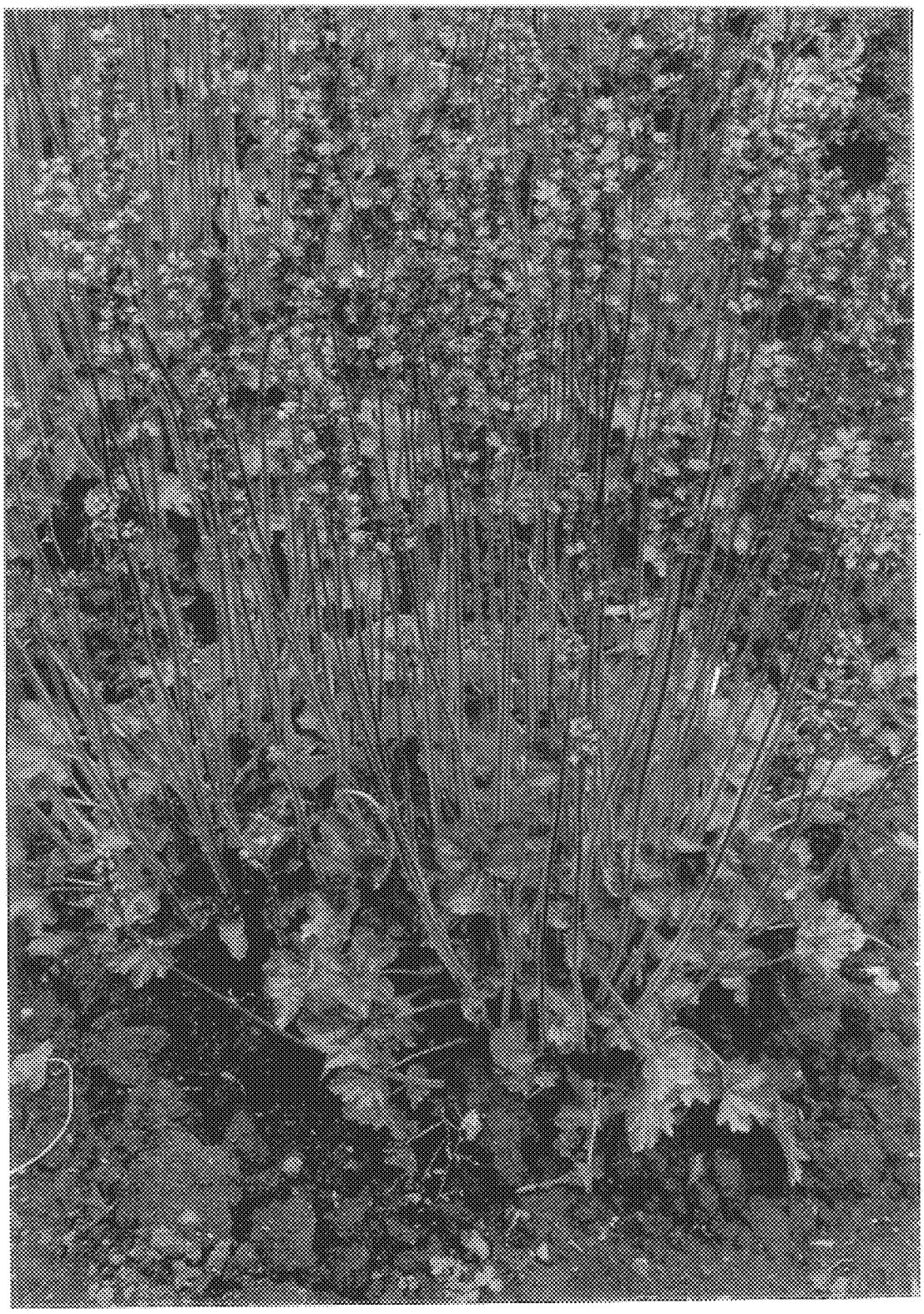
FIG. 2 illustrates the entire plant.

The drawings depict the plant as true to type as is photographically possible.

DETAILED PLANT DESCRIPTION

The following is a detailed description of the new Heuchera hybrid based on observations of specimens in Canby, Oreg. The color descriptions are all based on *The Royal Horticultural Society Colour Chart* and the *American Rhododendron Society* publication, "A Contribution Toward Standardization of Color Names in Horticulture."

Foliage:
- *Type*.—Evergreen.
- *Shape*.—Rounded, cordate, 9-lobed.
- *Length*.—7.5 cm.
- *Width*.—8 cm. at widest point.

- *Petiole length*.—10–12 cm.
- *Margins*.—Lobed, ciliolate.
- *Apex*.—Broadly obtuse, lobed.
- *Base*.—Cordate.
- *Texture*.—Smooth, slightly pubescent.
- *Leaf arrangement*.—Basal leaves tufted.
- *Venation*.—Reticulate.

Flower:
- *Petal count*.—5.
- *Ovary*.—Partially inferior.
- *Carpels*.—2-celled.
- *Stamens*.—5.
- *Petal shape*.—Spatulate-truncate, slightly recurved, margin entire.
- *Flower type*.—Complete calyx tube, cylinder-shaped, margin entire.
- *Flower size*.—To 1 cm.
- *Flower number*.—Average 50 per panicle.
- *Peduncle width*.—4 mm tapering to 0.7 mm.
- *Peduncle texture*.—Hirsute.
- *Inflorescence width*.—4–5 cm.
- *Blooming habit*.—Hoary panicles to 50 cm.
- *Bloom period*.—April to June (in Oregon).
- *Fragrance*.—Not fragrant.
- *Lastingness*.—To 3 weeks (panicles on the plant). To 9 days (panicles off the plant).

Fruit:
- *Type*.—Dehiscent capsule.
- *Fertile*.—Fertile.

Size:
- *Height*.—15 cm (1-year-old plant grown in an 8-inch pot in Canby, Oreg.).
- *Width*.—42 cm (1-year-old plant grown in an 8-inch pot in Canby, Oreg.).

Disease: Plants grown in Canby, Oreg., show little susceptibility to diseases except for root rot when grown under wet conditions.

Hardiness: Cold tolerance is set at USDA Zone 4 (−34° to −29° C.). Upper heat tolerance is unknown.

Color Characteristics

Foliage:
- *Mature leaves, upper surface, spring/summer*.—R.H.S. 137A Green Group (Moderate Olive Green ARS) mottled with R.H.S. 148D Yellow Green Group (Grayish Yellow Green ARS).

*Upper surface, fall through winter*.—R.H.S. 139B Green Group (Moderate Yellowish Green ARS) mottled with R.H.S. 139D Green Group (Moderate Yellow Green ARS).

*Lower surface*.—R.H.S. 148D Yellow Green Group (Grayish Yellow Green ARS).

Flowers:

*Petal upper surfaces*.—R.H.S. Red Purple Group 57A (Vivid Red ARS) senescing to R.H.S. Red Purple Group 60A.

*Petal lower surfaces*.—R.H.S. Red Group 39B senescing to R.H.S. Red Purple Group 60A. Area around ovary: R.H.S. Red Group 36D.

Stamens: R.H.S. Orange Group 28A.

Peduncle: R.H.S. Yellow Green Group 146A becoming R.H.S. Red Purple Group 152A near the apex.

Fruit: R.H.S. Green Group 143B.

DESCRIPTION OF PARENT PLANTS

This hybrid has characteristics which make it unique from its parents. One parent was a Heuchera seedling selected for its large inflorescences and large flowers. However, flower color was poor. The other parent was a selected *H. sanguinea* seedling in the nursery with huge cerise flowers and attractively mottled foliage. Crossing of the aforementioned plants resulted in the instant cultivar displaying superior flower color, large flowers, dense inflorescences, and attractive mottled foliage. 'Raspberry Regal' (unpatented) is the closest Heuchera to the instant cultivar in commerce known to me but suffers from muddy flower color and non-distinctive foliage. (See Aileen Stocks, Saxifragaceae, published by the Hardy Plant Society (ISBN 901687 111), p. 36.)

I claim:

1. A new and distinct hybrid of Heuchera plant substantially as shown and described, characterized by unique flower panicles, attractive leaf coloration, and large flowers.

* * * * *